US00PP23348P2

(12) United States Plant Patent
van Noort

(10) Patent No.: US PP23,348 P2
(45) Date of Patent: Jan. 22, 2013

(54) ***ECHINACEA* PLANT NAMED 'PICCOLINO'**

(50) Latin Name: *Echinacea purpurea*
Varietal Denomination: Piccolino

(76) Inventor: Marco van Noort, Warmond (NL)

( * ) Notice: Subject to any disclaimer, the term of this patent is extended or adjusted under 35 U.S.C. 154(b) by 103 days.

(21) Appl. No.: 13/068,520

(22) Filed: May 13, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu
(74) *Attorney, Agent, or Firm* — Penny J. Aguirre

(57) ABSTRACT

A new cultivar of hybrid *Echinacea*, 'Piccolino', characterized by its anemone-type (semi-double) inflorescences with ray florets and disk florets that are deep red-purple in color, its stems that are strong and held upright, its floriferous habit, and it compact and short plant habit.

2 Drawing Sheets

Botanical classification: *Echinacea purpurea.*
Variety denomination: 'Piccolino'.

BACKGROUND OF THE INVENTION

The present Invention relates to a new and distinct cultivar of *Echinacea purpurea* and will be referred to hereafter by its cultivar name, 'Piccolino'. 'Piccolino' represents a new purple coneflower, an herbaceous perennial grown for landscape use.

The new cultivar arose from an ongoing breeding program conducted by the Inventor in a designated field at his nursery in Warmond, The Netherlands. The goal of his breeding program is to create new cultivars of *Echinacea* that exhibit a short and firm plant habit combined with inflorescences with attractive form and coloration. The Inventor made a cross in summer of 2008 between unnamed proprietary plants of *Echinacea purpurea* from his breeding line. 'Piccolino' was selected by the Inventor as a single unique plant amongst the resulting seedlings from the above cross in September of 2009.

Asexual reproduction of the new cultivar was first accomplished by division in Warmond, The Netherlands in October of 2008 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Piccolino' as a unique cultivar of *Echinacea.*

1. 'Piccolino' exhibits a compact and short plant habit.
2. 'Piccolino' exhibits strong, upright stems.
3. 'Piccolino' is very floriferous.
4. 'Piccolino' exhibits anemone-type inflorescences (semi-double) with ray florets and disk florets that are deep red-purple in color; disk florets exhibit an enlarged petal.

The female parent differs from 'Piccolino' in having weaker stems and in having single inflorescences. The male parent differs from 'Piccolino' in having a less compact and taller plant habit, in having weaker stems, and in having inflorescences that are less intense in color. 'Piccolino' can be most closely compared to the cultivars 'Razzmatazz' (U.S. Plant Pat. No. 13,894) and 'Irresistible' (U.S. Plant Pat. No. 20,756). Both are similar to 'Piccolino' in having semi-double inflorescences. 'Razzmatazz' differs from 'Piccolino' in having a taller plant height, a less compact plant habit, and in being considerably less floriferous. 'Irresistible' differs from 'Piccolino' in having a less compact and taller plant habit and in having inflorescences that are orange to red-orange in color.

BRIEF DESCRIPTION OF THE DRAWING

The plants and plant parts in the accompanying photographs depict a one year-old plant of 'Piccolino' as field grown outdoors in Warmond (containerized for the photographs), The Netherlands.

The photograph in FIG. 1 provides a side view of 'Piccolino' in bloom.

Figure 1:
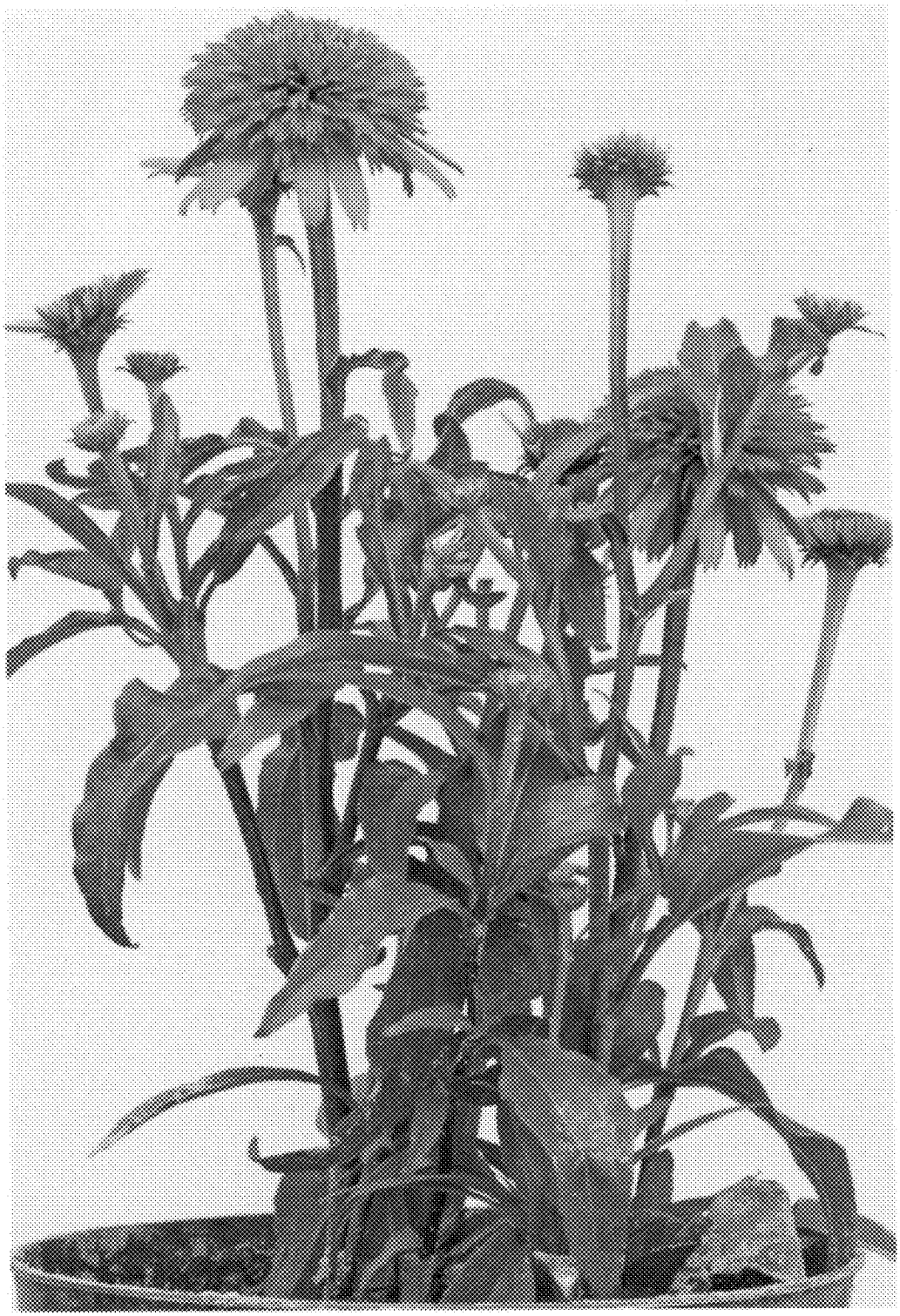
Figure 2:
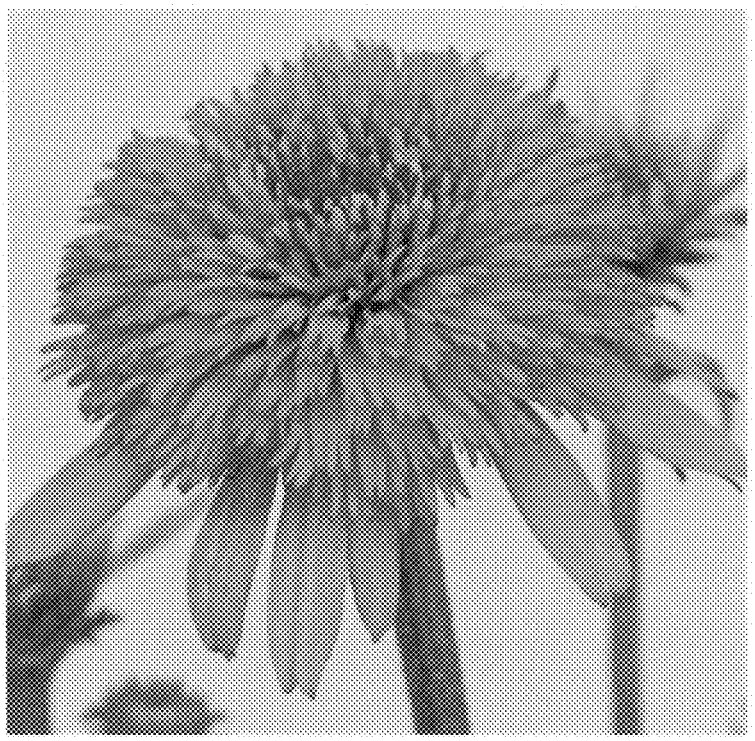

The photograph in FIG. 2 shows a close-up of an inflorescence of 'Piccolino'.

Figure 3:
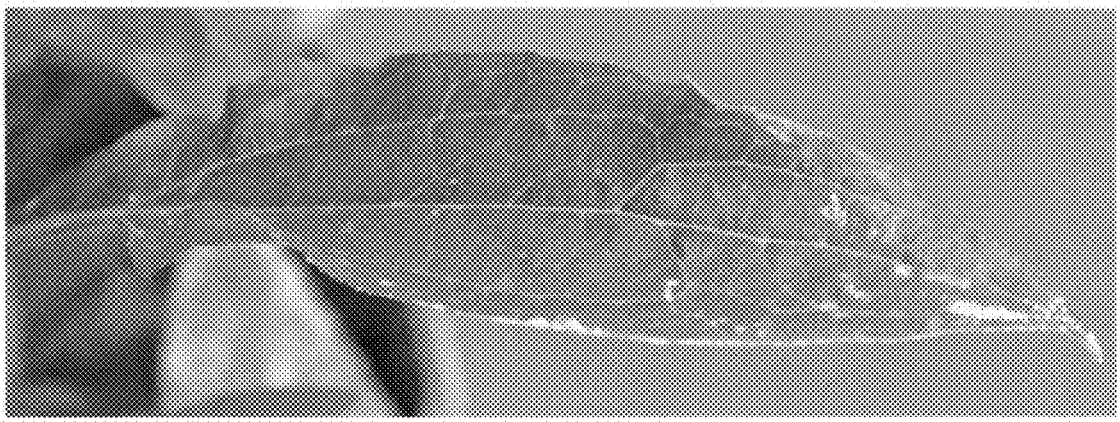

The photograph in FIG. 3 provides a close-up view of a leaf of 'Piccolino'. The colors in the photograph may differ slightly from the color values cited in the detailed botanical description, which accurately describe the colors of the new *Echinacea.*

BOTANICAL DESCRIPTION OF THE PLANT

The following is a detailed description of a one-year-old plant of the new cultivar as grown outdoors in a test garden in Warmond, The Netherlands. The plants were grown under average day temperatures of 10° to 22° C. and average night temperatures of 4° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early July to late September in The Netherlands.

*Plant habit.*—Herbaceous perennial, clump forming, upright.

*Height and spread.*—Reaches about 30 cm in height and spread.

*Hardiness.*—U.S.D.A. Zones 3 to 9.

*Diseases resistance.*—No particular resistance or susceptibility has been observed.

*Root description.*—Fibrous.

Growth and propagation:

*Propagation.*—Division, vegetative stem cuttings, and tissue culture.

*Growth rate.*—Moderately vigorous.

Stem description:

*Shape.*—Slightly oval, solid.

*Stem color.*—146A but darker and heavily tinged with 166A.

*Stem size.*—An average of 7 mm in diameter and 20 cm in height excluding peduncles.

*Stem strength.*—Very strong.

*Stem aspect.*—Held upright.

*Stem surface.*—Moderately rough to touch and sparsely covered with short strigose hairs about 1 mm in length and NN155C to NN155D in color.

*Stem number.*—Average of 4 main stems.

*Internode length.*—Average of 4.7 cm in length.

*Branching.*—Main flowering stem with an average of 4 lateral branches.

Foliage description:

*Leaf shape.*—Narrowly ovate.

*Leaf division.*—Simple.

*Leaf base.*—Attenuate to narrowly cuneate.

*Leaf apex.*—Narrowly acute.

*Leaf venation.*—Pinnate, 145A to 145B on upper surface and 145C on lower surface.

*Leaf margins.*—Entire and undulate.

*Leaf attachment.*—Petiolate on lower leaves and sessile on upper leaves.

*Leaf arrangement.*—Alternate.

*Leaf size.*—Average of 10.6 cm in length and 3.3 cm in width.

*Leaf color.*—Newly formed upper surface; ranges from 143A to 144A, newly formed lower surface; 143A, mature upper surface; N137C, mature lower surface; ranges from 137C or 147B.

*Leaf surface.*—Upper surface is moderately glossy, lower surface is slightly glossy, both surfaces are moderately covered with short strigose hairs about 0.3 mm in length and 155C to 155D in color.

*Petioles.*—V-shaped, an average of 2.3 cm in length and 3 mm in width, ranges from 145A to 145B in color on upper surfaces and 144A to 144B on lower surface, and 137A on margins, surface is pubescent.

Flower description:

*Type.*—Capitulum, heterogamous with ray florets around the head margin and disk florets with expanded ray floret-like petal, anemone-type (referred to as semi-double).

*Capitulum number.*—An average of 5 per stem.

*Lastingness of inflorescence.*—About 2 to 3 weeks.

*Capitulum size.*—Matures to about 5.2 cm in depth and 7.3 cm in diameter, disk is about 6.5 cm in diameter.

*Fragrance.*—Very faint, acid-sweet, pleasant.

*Involucral bracts or phyllary.*—About 48 arranged in 2 overlapping rows, average of 6 mm in length and 3 mm in width, cuneate base, acute apex, ovate in shape, upper surface is 137B in color, lower surface ranges from 143A to 143C in color, margins entire and sparsely covered with short hairs about 0.3 mm in length and 155C in color, surface is dull and smooth on both surfaces.

*Buds.*—Flattened globular in shape, an average of 4.6 cm in diameter and 1.6 cm in height, color 144A with spines ranging from N167A to N167B and immature ray florets ranging from 174A to 174B.

*Peduncle.*—Strong, terminal is an average of 8.9 cm in length and 5 mm in diameter with axillary peduncles ($4^{th}$) an average of 6.8 cm in length and 5 mm in diameter, terminals held upright with axillary peduncle held at an average angle of 30° to vertical, darker than 146A in color, surface is sparsely covered with short strigose hairs about 1 mm in length and NN155C in color.

*Ray florets* (*sterile*).—Average of 14 in single row, narrow oblanceolate in shape, smooth and moderately ridged (carinate) on both surfaces, about 3.9 cm in length and 8 mm in width, praemorse apex, cuneate base, entire margin except apex, smooth and dull surface on both surfaces, reflexed as they mature to about 40° from horizontal, color of upper surface when opening; 64B, color of lower surface when opening; 60B to 60C with tips tinged with 146A to 146B, color of upper surface when fully open; 64B, color of lower surface when mature; ranges from 60B to 60C with tips tinged with 146B, non fading.

*Disk flowers* (*bisexual*).—Numerous, about 250, tubular in shape with one petal expanded like a ray floret, arranged spirally on receptacle, apex is praemorse, fused base, entire margin, average of 2.4 cm in length and 6 mm in width, surface of upper surface is smooth and dull, surface of lower surface is smooth and slightly glossy, color when opening upper surface; ranges from 63A to 63B, color of lower surface when opening; ranges from 59C to 59D with base tinged with 146B to 146C, color of upper surface when fully open; ranges from 61A or 63A to 63B, color of lower surface when fully open; 59C to 59D with base tinged with 146B to 146C.

*Disk spines.*—Average of 250, acicular in shape, acute apex, attenuate base, smooth and glossy surface, color is N34A at apex, 143B in mid region and 145B at base.

*Receptacle.*—Globular in shape, an average of 1 cm in height and 1.3 cm in diameter, and 155C or 157D in color.

Reproductive organs (present on disk florets only):

*Gynoecium.*—Pistil; 1, 6 mm in length, style; about 5 mm in length and 156C in color, stigma; unequal, decurrent and 59A to 59B in color, ovary; 157D in color.

*Androcoecium.*—Stamens; 4, filaments; 2 mm in length and 156D in color, anthers; oblong in shape, about 1 mm in length and N199A in color, pollen; none observed.

*Fruit/seed.*—No seed production has been observed.

It is claimed:

1. A new and distinct cultivar of *Echinacea* plant named 'Piccolino' substantially as herein illustrated and described.

* * * * *